United States Patent [19]
Jersak et al.

[11] 4,053,527
[45] Oct. 11, 1977

[54] MANUFACTURE OF HALONITROBENZENES
[75] Inventors: Ulrich Jersak; Horst Scheuermann, both of Ludwigshafen, Germany
[73] Assignee: BASF Aktiengesellschaft, Ludwigshafen, Germany
[21] Appl. No.: 772,283
[22] Filed: Feb. 25, 1977

Related U.S. Application Data
[63] Continuation-in-part of Ser. No. 737,723, Nov. 1, 1976.
[30] Foreign Application Priority Data
Dec. 11, 1975 Germany .............................. 2555736
[51] Int. Cl.$^2$ .............................................. C07C 79/12
[52] U.S. Cl. .................................................... 260/646
[58] Field of Search ......................................... 260/646

[56] References Cited
FOREIGN PATENT DOCUMENTS
732,634  4/1966  Canada ................................. 260/646

Primary Examiner—Leland A. Sebastian
Attorney, Agent, or Firm—Keil, Thompson & Shurtleff

[57] ABSTRACT

Halonitrobenzenes are manufactured by reacting halonitroanilines with alkanols and nitrosating agents in the presence of water and an acid at not less than 35° C. The products are starting materials for the manufacture of pharmaceuticals, dyes and pesticides.

14 Claims, No Drawings

MANUFACTURE OF HALONITROBENZENES

CROSS REFERENCE TO RELATED APPLICATION

The subject application is a continuation-in-part of application Ser. No. 737,723, which was filed on Nov. 1, 1976.

BACKGROUND OF THE INVENTION

The present invention relates to a new process for the manufacture of halonitrobenzenes by reacting halonitroanilines with alkanols and nitrosating agents in the presence of water and an acid at not less than 35° C.

Houben-Weyl, Methoden der Organischen Chemie, Volume 10/3, pages 116 et seq. discloses that aromatic diazonium salts, in alcohols, can be converted to the corresponding aromatic hydrocarbons by heating; it is recommended to use as concentrated a solution of the diazonium salt as possible and to add to the solution from 5 to 10 times its volume of the alcohol. In the reaction, the alcohol is converted to the corresponding aldehyde and the resulting increase in aldehyde content prevents re-use of the unconverted alcohol. Depending on the structure of the diazonium salt, the reaction must either be carried out under anhydrous conditions or an 80 percent strength by weight aqueous ethanol solution can be used. Organic Reactions, Volume II, page 274 (Wiley, N.Y.) also teaches that whilst it is not absolutely essential to carry out the reaction under anhydrous conditions, the amount of water should be restricted to from about 5 to 10%.

In addition to the hydrocarbons, the phenol ethers corresponding to the alcohol used, and greater or lesser amounts of resin (Houben-Weyl, loc. cit., pages 123 and 124) are formed as by-products, especially if the reaction is carried out with alcohol diluted with water. The yield and purity of the end products of these processes are in most cases unsatisfactory, particularly in industrial operation. Thus, for example, the yield of end product is stated to be 46% when 2,4-dichloroaniline is used as the amine starting material and 53% when anthranilic acid is used as the amine starting material (Houben-Weyl, loc. cit., page 125). An article in Angewandte Chemie, 70 (1958), 211, discloses that instead of alcohols, ethers such as dioxane must be used to avoid the formation of by-products and to improve the yield of end product. Equally, it is possible, instead of using the aqueous diazotization solution, to isolate the diazonium salt itself and to react it with the alcohol (Sounders, "The Aromatic Diazocompounds"(E. Arnold & Co., London 1949), page 271). All these processes are unsatisfactory, particularly in industrial operation, in respect of economy and simplicity of operation and yield of end product.

An article in Science, 117 (1953), 379 - 380 discloses that the reaction of the benzenediazonium salt with an alcohol in most cases leads to the corresponding phenyl alkyl ether and not to the benzene derivative which remains after elimination of the diazonium group, or only to minor amounts of this derivative. This is also disclosed in H. Zollinger, Azo and Diazo Chemistry, Interscience Publishers, New York and London, 1961, page 141. Houben-Weyl also points out (loc. cit., page 124) that the decomposition of numerous diazonium salts by heating in ethanol results in replacement of the diazonium group by the ethoxy radical. According to this disclosure, replacement of the diazonium group by hydrogen requires certain reaction conditions, such as the addition of zinc, or irradiation with ultraviolet light. To achieve higher yields of benzenes from the reduction with alcohols, it is recommended to add alkalis or copper compounds or zinc compounds (loc. cit., pages 119 and 127). Houben-Weyl points out (loc. cit., page 128) that with increasing temperature the ratio of the two reaction products, namely the phenol ether and the hydrocarbon, shifts in favor of the former. Since the product mixtures are often difficult to work up, and the yield of the desired hydrocarbon is poor, the use of other reducing agents is recommended (Zollinger, loc. cit., page 168).

J. Amer. Chem. Soc., 72 (1950), 798, discloses that 2,6-dichloro-4-nitroaniline, ethanol and sodium nitrite can be reacted at the boil, in the absence of water and in the presence of concentrated sulfuric acid, to give 3,5-dichloronitrobenzene in a yield of 84%. A corresponding reaction to give the 3,5-dibromo derivative gives a yield of 91%. The process is unsatisfactory in respect of yield and purity of the end product and simple, reliable and economical operation, especially on an industrial scale.

BRIEF DESCRIPTION OF THE INVENTION

It is an object of the present invention to provide a new process by means of which halonitrobenzenes can be manufactured more simply and more economically, in better yield and higher purity, particularly in industrial operation.

We have found that this object is achieved and that halonitrobenzenes of the formula

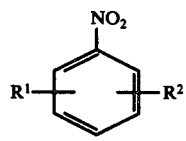

I where $R^1$ and $R^2$ may be identical or different and each is halogen and $R^2$ may also be hydrogen, are obtained in an advantageous manner by reacting halonitroanilines with alcohols and nitrosating agents at elevated temperatures in the presence of an acid, when halonitroanilines of the formula

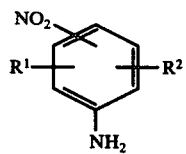

II where $R^1$ and $R^2$ have the above meanings, are reacted with aliphatic, cycloaliphatic or araliphatic alcohols at not less than 35° C, in the presence of water. The amount of water present in the reaction mixture can vary widely from as little as about 0.5 moles per mole of starting material II up to as much as about 1,000 moles of water per mole of starting material II.

If sodium nitrite, 2,6-dichloro-4-nitro-aniline, sulfuric acid and ethanol are used, the reaction can be represented by the following equation:

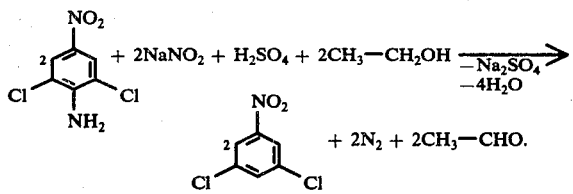

Compared to the prior art, the process of the invention gives halonitrobenzenes more simply and more economically, in better yield and higher purity, particularly on an industrial scale. It is not necessary to add copper salts or other catalysts, or large amounts of alcohol. The amount of halonitrophenol formed is less than 0.06 percent by weight, based on the reaction mixture, in spite of the high water content of the latter. Significant formation of resinous by-products is not observed. All these advantageous results are surprising, specifically in view of the fact that the above publications teach that the diazonium salt should first be produced in the cold, by the conventional method of diazotization, and the reduction with alcohol should then be carried out in the absence of water, or in the presence of minimal amounts of water, using assistants such as copper salts. In view of the disclosure in Houben-Weyl, it was also unexpected that the end product is obtained in better yield and higher purity though the diazonium salt is not separately prepared beforehand and though the reaction is carried out in the presence of substantial amounts of water, at elevated temperatures.

Preferred starting materials II and, accordingly, preferred end products I are those where $R^1$ and $R^2$ are identical or different and each is iodine or, advantageously, bromine or, especially, chlorine, and $R^2$ may also be hydrogen. The halonitroanilines may contain the nitro group and/or the two halogen atoms in any desired position of the nucleus; preferably, the substituents are in the 2-, 4- or 6-position. Examples of suitable starting materials II are: 2-chloro-4-nitro-aniline, 2-bromo-4-nitro-aniline, 2-iodo-4-nitro-aniline, 2,6-dichloro-4-nitro-aniline, 2,6-dibromo-4-nitro-aniline, 2,6-diiodo-4-nitro-aniline, 2-chloro-6-bromo-4-nitro-aniline, 2-chloro-6-iodo-4-nitro-aniline, 2-bromo-6-iodo-4-nitro-aniline, 4-chloro-2-nitro-aniline, 6-chloro-2-nitro-aniline, 4-bromo-2-nitro-aniline, 6-bromo-2-nitro-aniline, 4-iodo-2-nitro-aniline, 4,6-dichloro-2-nitro-aniline, 4,6-dibromo-2-nitro-aniline, 4,6-diiodo-2-nitro-aniline, 4-chloro-6-bromo-2-nitro-aniline, 4-bromo-6-chloro-2-nitro-aniline, 4-chloro-6-iodo-2-nitro-aniline, 4-iodo-6-chloro-2-nitro-aniline, 4-bromo-6-iodo-2-nitro-aniline and 4-iodo-6-bromo-2-nitro-aniline. 2,6-Dihalo-4-nitro-anilines and 2,4-dihalo-6-nitro-anilines, especially 2,6-dibromo-4-nitro-aniline, 2,4-dibromo-6-nitro-aniline, 2,6-dichloro-4-nitro-aniline and 2,4-dichloro-6-nitro-aniline are preferred.

The starting materials II are reacted in stoichiometric amounts or using an excess of alcohol, preferably using from 3 to 30, especially from 5 to 15, equivalents (moles divided by the number of hydroxyl groups in the molecule) of alcohol per mole of starting material II. The alcohols may be aliphatic, cycloaliphatic or araliphatic monoalcohols or polyalcohols. Preferred alcohols are those of the formula

$$R^3OH \qquad\qquad III$$

where $R^3$ is alkyl of 1 to 5 carbon atoms or cyclohexyl, or aralkyl of 7 to 12 carbon atoms or HO—$R^4$—, where $R^4$ is an aliphatic radical, especially alkylene of 2 to 4 carbon atoms, or $R^3$ is $R^5O$—$(R^4O)_n$—$R^4$—, where the individual $R^4$'s may be identical or different and each is an aliphatic radical, especially alkylene of 2 to 4 carbon atoms, and $R^5$ is hydrogen or an aliphatic radical, especially alkyl of 1 to 4 carbon atoms, and $n$ is 4, 3, 2 or especially 1. The above radicals may furthermore be substituted by groups which are inert under the reaction conditions, e.g. alkyl or alkoxy each of 1 to 3 carbon atoms.

Examples of suitable alcohols III are methanol, ethanol, n- and i-propanol, n-butanol, butan-2-ol, isobutanol, ethylene glycol, diethylene glycol, methylethylene glycol, benzyl alcohol, n-pentanol, phenylethanol, neopentylglycol, p-methylbenzyl alcohol, p-ethoxybenzyl alcohol, 1,3-propylene glycol, 1,4-butanediol, 1,2-propylene glycol, triethylene glycol, diethylene glycol mono-n-butyl ether or appropriate mixtures. Ethanol, isopropanol, methylethylene glycol, n-propanol and isobutanol are preferred.

In addition, the reaction employs nitrosating agents, e.g. nitrous acid and compounds which are converted to nitrous acid under the reaction conditions, e.g. nitrous gases, salts, preferably alkali metal salts, of nitrous acid, especially potassium nitrite and sodium nitrite, and esters of nitrous acid, advantageously cycloalkyl nitrites, aralkyl nitrites or, preferably, alkyl nitrites. If alkyl nitrites are used, the addition methyl alcohol can be dispensed with entirely or, advantageously, partially, since such nitrites can, under the reaction conditions, act as a replacement for a combination of nitrous acid and the corresponding alcohol; in such cases, it is advantageous to use a ratio of from 1 to 5 equivalents of alcohol per mole of starting material II. Preferred esters are alkyl nitrites of 1 to 6 carbon atoms, e.g. ethyl nitrite, n-propyl nitrite, n-isopropyl nitrite, n-butyl nitrite, isobutyl nitrite, sec.-butyl nitrite, tert.-butyl nitrite, amyl nitrite, isoamyl nitrite, benzyl nitrite, cyclohexyl nitrite and especially methyl nitrite. For the purposes of the invention, nitrous gases are the nitrogen oxides conventionally used as nitrosating agents, namely nitrogen monoxide, nitrogen dioxide, nitrogen tetroxide and dinitrogen trioxide. They may be used individually, or, preferably, as an appropriate mixture, advantageously of nitrogen monoxide and nitrogen dioxide. In general, from 1.1 to 5 moles of alkyl nitrite, other nitrous acid esters and/or nitrous gases are used per mole of starting material II, advantageously from 1.1 to 2.7, especially from 1.1 to 1.7, moles of alkyl nitrite or other nitrous acid esters, or from 1.5 to 5, especially from 2 to 4 moles of $N_2O_3$, per mole of starting material II. Gases which are inert under the reaction conditions, e.g. nitrogen, can be admixed to the said nitrogen oxides or gas mixtures.

Further possible reagents are glycol esters of nitrous acid. These esters of nitrous acid may be produced in any desired manner, advantageously in accordance with the process disclosed in German Laid-Open Application DOS 2,144,420, where glycols or glycol derivatives are reacted with nitrous acid or nitric oxides. Preferred esters of glycols and glycol derivatives are monoglycol or diglycol esters of nitrous acid, of the formula $$ONO-R^6-X \qquad\qquad IV$$

where $R^6$ is —$R^7$—O— or

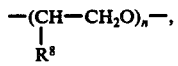

$R^7$ is an aliphatic radical and $R^8$ is hydrogen or an aliphatic radical, $n$ is 1, 2, 3 or 4 and X is —NO or an aliphatic, araliphatic, cycloaliphatic or aromatic radical. Advantageously, $R^7$ is alkylene of 3 to 12, especially 4 to 9, carbon atoms, $R^8$ is hydrogen or alkyl of 1 to 4 carbon atoms, especially methyl, $n$ is 1, 2 or 3 and X is —NO, alkyl of 1 to 4 carbon atoms, aralkyl of 7 to 12 carbon atoms, cyclohexyl, cyclopentyl, phenyl or alkylcarbonyl of 2 to 5 carbon atoms, advantageously acetyl. The said alkyl and alkylene radicals may have straight or branched chains. The above preferred radicals may furthermore be substituted by groups which are inert under the reaction conditions, e.g. alkoxy or alkyl each of 1 to 3 carbon atoms. In general, from 1.1 to 5 moles, advantageously from 1.1 to 2.7 moles, and especially from 1.1 to 2.2 moles, of monoglycol ester of nitrous acid are employed per mole of starting material II. Accordingly, from 0.55 to 2.5, advantageously from 0.55 to 1.35, and especially from 0.55 to 1.1 moles of diglycol ester of nitrous acid are employed per mole of starting material II. Examples of suitable esters IV are monoesters and diesters of nitrous acid with the following compounds:

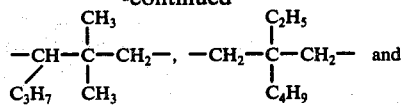

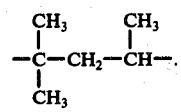

The reaction is carried out in the presence of water, advantageously of from 5 to 100, especially from 15 to 50, moles of water per mole of starting material II; the water may be added separately and/or in the form of aqueous solutions of the reactants, e.g. of aqueous acid, aqueous alkali metal nitrite solutions or mixtures of the alcohol with water. The water formed in the reaction itself is not defined as added water in the present context and is not included in the amounts of water stated above to be advantageous.

The reaction is carried out in the presence of an acid, advantageously in an amount of from 1.5 to 15, especially from 2.5 to 10, equivalents, based on starting material II. In general, inorganic acids are used. In place of monobasic acids, equivalent amounts of polybasic acids may be employed. Examples of suitable acids are hydrogen chloride, hydrogen bromide, hydrogen io-

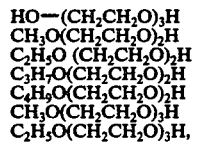

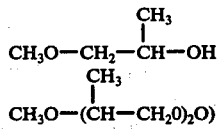

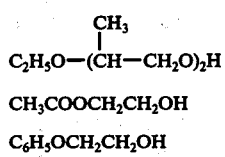

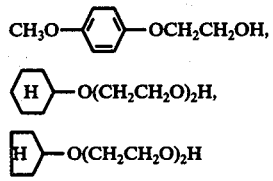

$C_2H_5O(CH_2CH_2O)_4H$, and diglycol esters where $R^6$ is —$R^7$—O—, X is —NO and $R^7$ is one of the alkylene radicals

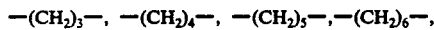

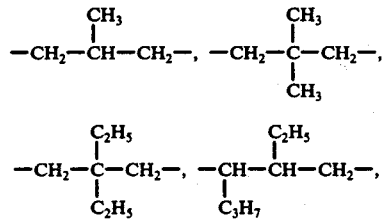

dide, perchloric acid, sulfuric acid, nitrous acid, phosphoric acid, nitric acid, boron-containing acids, e.g. boric acid and fluoboric acid, or appropriate mixtures. The acids may be used in a concentrated form, as mixtures with one another and/or as mixtures with a solvent, especially with water. Sulfuric acid, nitric acid, phosphoric acid and perchloric acid are preferred.

The reaction is carried out at not less than 35° C, as a rule at from 35° C to the boiling point of the mixture, advantageously at from 40° to 200° C and preferably at from 45° to 100° C, under atmospheric or superatmospheric pressure, continuously or batchwise. As a rule, components of the starting mixture, e.g. water, alcohol or acid, or the total starting mixture, serve as the solvent medium for the reaction.

The reaction may be carried out as follows: a mixture of starting material II, alcohol, nitrosating agent, acid and water is kept at the reaction temperature for from 1.5 to 5 hours. Advantageously, the nitrosating agent, e.g. the aqueous sodium nitrite solution or the nitrous acid ester, is run into the mixture of the reactants. The rate of addition may be varied within wide limits. In most cases, the end of the reaction coincides with the end of the addition of the nitrosating agent. The end product is isolated from the reaction mixture by conventional methods, e.g. by filtration.

The compounds which may be manufactured by the process of the invention are valuable starting materials for the manufacture of pharmaceuticals, dyes and pesticides. With regard to their use, reference may be made to the above publications and to Ullmanns Encyklopadie der technischen Chemie, Volume 12, pages 798 – 800.

In the Examples, parts are by weight.

EXAMPLE 1

207 parts of 2,6-dichloro-4-nitro-aniline are introduced into 180 parts of isopropanol and 300 parts of water and 200 parts of concentrated sulfuric acid (98 percent strength by weight) are then added to the mixture. A solution of 125 parts of $NaNO_2$ in 175 parts of water is run in at 50° C, resulting in the evolution of nitrogen. The mixture is cooled, 400 parts of water are added and the product is filtered off. 192 parts (a practically quantitative yield) of 3,5-dichloro-nitro-benzene, of melting point 60°-62° C, are obtained.

EXAMPLE 2

If the reaction is carried out as described in Example 1, but with 130 parts of isopropyl nitrite instead of $NaNO_2$, 186 parts (97% of theory) of 3,5-dichloro-nitro-benzene, of melting point 61°-62° C, are obtained.

EXAMPLE 3

207 parts of 4,6-dichloro-2-nitro-aniline are introduced into 400 parts of ethanol and 900 parts of water, and 400 parts of concentrated sulfuric acid (98 percent strength by weight) are then added to the mixture. A solution of 105 parts of $NaNO_2$ in 175 parts of water is run in at 80° C, as described in Example 1. The mixture is cooled and the product is filtered off. 182 parts (95% of theory) of 3,5-dichloro-nitro-benzene, of melting point 56°-59° C, are obtained.

EXAMPLE 4

296 parts of 2,6-dibromo-4-nitro-aniline are introduced into 400 parts of isopropanol and 750 parts of water and 130 parts of concentrated sulfuric acid (98 percent strength by weight) are then added to the mixture. A solution of 105 parts of $NaNO_2$ in 150 parts of water is run in at 70° C as described in Example 1. The mixture is cooled, 300 parts of water are added and the product is filtered off. 278 parts of 3,5-dibromo-nitro-benzene (99% of theory), of melting point 102°-104° C, are obtained.

EXAMPLE 5

207 parts of 2,6-dichloro-4-nitro-aniline are introduced into 500 parts of glycol monomethyl ether and 1,000 parts of 50 percent strength by weight sulfuric acid are then added to the mixture. 90 parts of $NaNO_2$ in 150 parts of water are added slowly at 70° C. The mixture is cooled and the product is filtered off. 179 parts (92% of theory) of 3,5-dichloro-nitro-benzene, of melting point 56°-59° C, are obtained.

EXAMPLE 6

103.5 parts of 2,6-dichloro-4-nitro-aniline and 103.5 parts of 2,4-dichloro-6-nitro-aniline are introduced into 180 parts of isopropanol and 300 parts of water, and 200 parts of concentrated sulfuric acid (98 percent strength by weight) are then added to the mixture. A solution of 125 parts of $NaNO_2$ in 175 parts of water is run in at 50° C, as described in Example 1. The mixture is cooled, 400 parts of water are added and the product is filtered off. 192 parts (a practically quantitative yield) of 3,5-dichloro-nitro-benzene, of melting point 60°-61° C, are obtained.

EXAMPLE 7

172.5 parts of 2-chloro-4-nitro-aniline are introduced into 180 parts of isopropanol and 300 parts of water, and 200 parts of concentrated sulfuric acid (98 percent strength by weight) are then added to the mixture. A solution of 125 parts of $NaNO_2$ in 175 parts of water is run in at 50° C, as described in Example 1. The mixture is cooled, 400 parts of water are added and the product is filtered off. 142 parts (90% of theory) of 3-chloro-nitro-benzene, of melting point 40°-42° C, are obtained.

EXAMPLE 8

207 parts of 2,6-dichloro-4-nitro-aniline are introduced into 500 parts of isopropanol, and 780 parts of 65 percent strength by weight nitric acid are then added to the mixture. A solution of 125 parts of $NaNO_2$ in 175 parts of water is run in at 50° C, as described in Example 1. The mixture is cooled, 400 parts of water are added and the product is filtered off. 172 parts (90% of theory) of 3,5-dichloro-nitro-benzene, of melting point 55°-57° C, are obtained.

EXAMPLE 9

207 parts of 2,6-dichloro-4-nitroaniline is introduced into 300 parts of isopropanol and 9 parts of water; 200 parts of concentrated (98 wt%) sulfuric acid is then added to the mixture. At 50° C, 170 parts of isopropyl nitrite is run in, nitrogen being evolved. The mixture is cooled, 800 parts of water is added, and suction filtration carried out. There is obtained 188 parts (98% of theory) of 3,5-dichloronitrobenzene, m.p.: 59° – 62° C.

EXAMPLE 10

207 parts of 2,6-dichloro-4-nitroaniline is introduced into 1,800 parts of isopropanol and 18,000 parts of water; 700 parts of concentrated (98 wt%) sulfuric acid is then added. At 60° C, a solution of 140 parts of sodium nitrite in 240 parts of water is slowly run in. The mixture is cooled and suction filtered. There is obtained 190 parts (99% of theory) of 3,5-dichloronitrobenzene, m.p.: 61° – 62°.

We claim:
1. A process for the manufacture of halonitrobenzenes of the formula

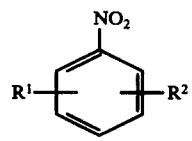

I where $R^1$ and $R^2$ may be identical or different and each is halogen, and $R^2$ may also be hydrogen, by reacting halonitroanilines with alcohols and nitrosating agents at elevated temperatures in the presence of an acid, wherein halonitroanilines of the formula

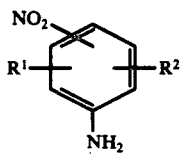

where $R^1$ and $R^2$ have the above meanings, are reacted with aliphatic, cycloaliphatic or araliphatic alcohols, which may be partly or wholly combined with the nitrosating agent, at not less than 35° C, in the presence of water.

2. A process as set forth in claim 1 wherein the reaction is carried out in the presence of from about 0.5 to 1,000 moles of water per mole of starting material II.

3. A process as set forth in claim 1, wherein the reaction is carried out with from 3 to 30 equivalents of alcohol per mole of starting material II.

4. A process as set forth in claim 1, wherein the reaction is carried out with alcohols of the formula $$R^3OH \qquad \qquad III$$

where $R^3$ is alkyl of 1 to 5 carbon atoms or cyclohexyl, or aralkyl of 7 to 12 carbon atoms, or HO—$R^4$—, where $R^4$ is alkylene of 2 to 4 carbon atoms, or $R^3$ is $R^5O$—($R^4O)_n$—$R^4$—, where the individual $R^4$'s may be identical or different and each is alkylene of 2 to 4 carbon atoms, and $R^5$ is hydrogen or alkyl of 1 to 4 carbon atoms, and $n$ is 4, 3, 2 or 1, and the above radicals may furthermore be substituted by alkyl or alkoxy each of 1 to 3 carbon atoms.

5. A process as set forth in claim 1, wherein the reaction is carried out with from 1.1 to 5 moles of alkyl nitrite, other nitrous acid esters and/or nitrous gases per mole of starting material II.

6. A process as set forth in claim 1, wherein the reaction is carried out with from 1.1 to 1.7 moles of alkyl nitrite or other nitrous acid esters or with from 1.5 to 5 moles of $N_2O_3$ per mole of starting material II.

7. A process as set forth in claim 1, wherein the reaction is carried out with from 1.1 to 5 moles of monoglycol ester per mole of starting material II.

8. A process as set forth in claim 1, wherein the reaction is carried out with from 1.1 to 2.7 moles of monoglycol ester per mole of starting material II.

9. A process as set forth in claim 1, wherein the reaction is carried out with from 0.55 to 2.5 moles of diglycol ester per mole of starting material II.

10. A process as set forth in claim 1, wherein the reaction is carried out with from 5 to 100 moles of water per mole of starting material II.

11. A process as set forth in claim 1, wherein the reaction is carried out with from 1.5 to 15 equivalents of acid, based on starting material II.

12. A process as set forth in claim 1, wherein the reaction is carried out at from 35° C to the boiling point of the mixture.

13. A process as set forth in claim 1, wherein the reaction is carried out at from 40° to 200° C.

14. A process as set forth in claim 1, wherein the reaction is carried out at from 45° to 100° C.